(12) United States Patent
Zybin (10) Patent No.: US 8,587,786 B2
(45) Date of Patent: Nov. 19, 2013

(54) METHOD FOR HIGH-RESOLUTION DETECTION OF NANOPARTICLES ON TWO-DIMENSIONAL DETECTOR SURFACES

(75) Inventor: Alexander Zybin, Dortmund (DE)

(73) Assignee: Leibniz—Institut für Analytische Wissenschaften—ISAS—e.V., Dortmuund (DE)

( * ) Notice: Subject to any disclaimer, the term of this patent is extended or adjusted under 35 U.S.C. 154(b) by 97 days.

(21) Appl. No.: 13/218,804

(22) Filed: Aug. 26, 2011

(65) Prior Publication Data

US 2011/0311962 A1     Dec. 22, 2011

Related U.S. Application Data

(63) Continuation-in-part of application No. PCT/EP2010/052229, filed on Feb. 23, 2010.

(30) Foreign Application Priority Data

Feb. 27, 2009   (DE) .......................... 10 2009 003 548

(51) Int. Cl.
*G01N 21/55* (2006.01)

(52) U.S. Cl.
CPC ..................................... *G01N 21/55* (2013.01)
USPC ......................................... 356/445; 356/448

(58) Field of Classification Search
CPC ..................................................... G01N 21/55
USPC .................................................. 356/445–448
See application file for complete search history.

(56) References Cited

U.S. PATENT DOCUMENTS

| | | | |
|---|---|---|---|
| 5,999,262 A * | 12/1999 | Dobschal et al. | 356/504 |
| 7,233,396 B1 | 6/2007 | Hall et al. | |
| 2009/0141376 A1* | 6/2009 | Smith et al. | 359/833 |

FOREIGN PATENT DOCUMENTS

| | | |
|---|---|---|
| DE | 4024476 | 2/1992 |
| DE | 102004033869 | 3/2006 |
| DE | 102005054495 | 5/2007 |
| DE | 102009003548 | 9/2010 |
| WO | WO0135081 | 5/2001 |
| WO | WO2010/097369 | 9/2010 |

OTHER PUBLICATIONS

Boecker et al; Differential Surface Plasmon Resonance Imaging for High-Troughput Bioanalyses; Anal. Chem.; 2007; pp. 702-709; vol. 79.

Chinowisky et al; Optical and Electronic Design for a High-Performance Surface Plasmon Resonance Imager; Proc. SPIE; Mar. 2004; pp. 173-182; vol. 5261.

(Continued)

*Primary Examiner* — Michael P Stafira
(74) *Attorney, Agent, or Firm* — Thorpe North & Western LLP (57) ABSTRACT

The invention relates to a surface plasmon resonance spectrometer comprising a radiation source that emits substantially monochromatic radiation, a sensor surface, an optical arrangement for lighting the sensor surface by the radiation emitted from the radiation source such that surface plasmons can be created in the sensor surface, a detector having a plurality of image elements and observation optics for depicting the radiation reflected by the sensor surface on the detector, characterized in that the resolution capability of the observation optics and of the detector is larger than the resolution that can be obtained by the deflection-limited radiation source.

13 Claims, 6 Drawing Sheets

(56) References Cited

OTHER PUBLICATIONS

Garini et al; From Mico to Nano: Recent Advances in High-Resolution Microscopy; Feb. 2005; pp. 3-12; vol. 16, No. 1.

Giebel et al; Imaging of Cell/Substrate Contacts of Living Cells with Surface Plasmon Resonance Microskopy; Biophysical J.; Jan. 1999; pp. 509-516; vol. 76.

Reinhard; Resolving Subdiffration-Limit Distance; SPIE Newsroom; Feb. 9, 2009; 3 pages.

Rong et al; Resolving Sub-Diffraction Limit Encounters in Nanoparticle Tracking Using Live Cell Plasmon Coupling Microscopy; Nano Letters; 2008; pp. 3386-3393; vol. 8, No. 10.

Snolyaninov et al; Novel Nanophotonics Geometries for Sensing Applications; Proc. Of SPIE; Aug. 2004; pp. 187-196; vol. 5554.

Zybin et al.; Real-time Detection of Single Immobilized Nanoparticles by Surface Plasmon Resonance Imaging; Plasmonics; 2010; pp. 31-35; vol. 5.

* cited by examiner

METHOD FOR HIGH-RESOLUTION DETECTION OF NANOPARTICLES ON TWO-DIMENSIONAL DETECTOR SURFACES

RELATED APPLICATIONS

This application is a continuation-in-part of International Application PCT/EP2010/052229 filed Feb. 23, 2010, and which specified the United States, and which is based on and claims priority to German Application DE 10 2009 003 548.6 filed Feb. 27, 2009.

TECHNICAL FIELD

The invention relates to a surface plasmon resonance microscope, comprising
(a) a radiation source emitting essentially monochromatic radiation,
(c) a sensor surface,
(b) an optical assembly for illuminating the sensor surface with the radiation emitted by the radiation source in such a way that surface plasmons are generated in the sensor surface,
(d) a detector with a plurality of detector elements, and
(e) an observation optical assembly for imaging the radiation reflected by the sensor surface on the detector.

The invention also relates to a method for the optical detection of individual nanoparticles bound to two-dimensional sensor surfaces or present near a two-dimensional sensor surface.

The sensor surface can be selectively coated with receptors or antibodies selectively binding viruses of a certain kind. Thereby, selectivity of the detection is ensured.

The resolution of optical assemblies, i.e. the ability to observe small objects in the optical microscopy, is limited by the diffraction. The smallest particles which can be resolved with a light optical microscope have a diameter in the range of 0.2 µm. The required assemblies are expensive.

Much smaller particles can be detected by means of electron microscopy. However, electron microscopy requires high vacuum. This is expensive and limits the application field of the method.

A label free method which enables the selective optical observation of viruses or interesting particles having a diameter in the range of few tens nanometers (nanoparticles) in water or in a buffer solution in-vivo is not known.

In the optical microscopy the change of the intensity of light at certain positions of the image is analyzed. If the observation is made with the human eye this is effected at the retina. A Charge Coupled Device (CCD) can be applied for the optoelectronic detection. As the changes are caused by the difference of optical properties of the object, such as transmission, diffraction index variations or the color with respect to the environment the properties of the object can thereby be characterized.

PRIOR ART

The publication "Imaging of Cell/Substrate Contacts of Living Cells with Surface Plasmon Resonance Microscopy" by K.-F. Giebel et al., Biophysical J. Vol. 76, 1999 p. 509-516 discloses a surface plasmon microscope.

The publication "Differential Surface Plasmon Resonance Imaging for High-Throughput Bioanalyses" by Boecker et al., Anal. Chem. 2007, Vol. 79, P. 702-709 discloses a surface plasmon microscope.

DE 10 2004 033 869 B3 discloses a method for the determination of surface plasmon resonances with two dimensional detection surfaces.

DE 40 24 476 C1 discloses a Kretschmann-assembly which is used for the determination of analyts in a fluid sample.

DE 10 2005 054 495 A1 discloses the use of distributed measurement and reference spots in surface plasmon resonance biosensors based on spatially resolved measurements. Application of multiple reference spots enable the correction of temperature variations. Common SPR-microscopy operates with predetermined spots at the sensor surface where an integrated measuring signal is detected. The spots usually have a size >100×100 µm². A required layer thickness of the molecules bound to the surface must be achieved in order to obtain a sufficient signal-to-noise ratio. Individual particles cannot be detected with this method because the signal integrated over a relative large area is detected.

In the publication "Optical and electronic design for a high-performance surface plasmon resonance imager" by Timothy M. Chinowsky, Tony Mctutis, Elain Fu and Paul Yager in Proc. SPIE Vol. 5261, Editor Brian M. Cullum March 2004, P. 173-182 a common SPR method is described using CCD-detectors.

The publications "Resolving sub diffraction-limit distances" by Björn M. Reinhard, Hongyun Wang, Guoxin Rong and Lynell Skewis in SPIE Newsroom. DOI: 10.1117/2.1200902.1452 and "Resolving Sub-Diffraction Limit Encounters in Nanoparticle Tracking Using Live Cell Plasmon Coupling Microscopy" of the same authors in Nano Letters 2008, Vol. 8, No. 10, P. 3386-3393 disclose methods for localized plasmon resonance in metallic nanoparticles.

The publication "From micro to nano: recent advances in high-resolution microscopy" by Y. Garini, B. J. Vermolen and I. T. Young in Current Opinion in Biotechnology, London, GB, LNKD-DOI:10.1016/J.Copbio.2005.01.003, Vol. 16, No. 11. February 2005, pages 3-12 discloses an overview of assemblies for the optical microscopy with particularly low detection limits related to the surface density of bound molecules. Various methods, including surface plasmon microscopy (SPR), are presented.

WO 01/35 081 A1 discloses a method and chemicals for improvement of surface plasmon spectroscopy.

The publication "Imaging of Cell/Substrate contacts of Living Cells with Surface Plasmon Resonance Microscopy" by K.-F. Giebel, C. Bechinger, S. Herminghaus, M. Riedel, P. Leiderer, U. Weiland and M. Bastmeyer in Biophysical Journal Vol. 76, 1999, P. 509-516 discloses the investigation of cell structures by means of conventional surface plasmon spectroscopy. The cell is present in a previously determined position and is and further comprising the cooperation with plasmons.

U.S. Pat. No. 7,233,396 B1 discloses a sensor for the determination of optical properties of a sample. Two beams with linearly polarized light where a phase difference is generated is used for this purpose.

DISCLOSURE OF THE INVENTION

It is an object of the invention to provide an assembly and a method of the above mentioned kind for optical detection of individual nanoparticles, especially of viruses, with higher resolution. According to the invention this object is achieved in that the resolution of the detector is higher than the diffraction-limited resolution which can be obtained with the radiation source achievable under classical conditions. Resolution is interpreted in this context as the ability to resolve the signal (particle) from a background signal. Surprisingly, it has been found that the observation of nanoparticles is possible which are much smaller than the light wavelengths. For example, it is possible to observe particles having a diameter of 40 nm even with a wavelength above 600 nm.

In order to provide the observation of nano particles, a high enough lateral resolution must be applied by imaging instead of integration of the signal over the sensor area. In order to avoid a situation where the signal disappears in the noise, preferably the background is corrected applying a reference image. The reference signal can be generated by calculating the average of the images, which are detected before binding a particle at the sensor surface.

The detection of plasmon resonance can be effected with a so-called Kretschmann-assembly. A local change of the reflectivity is caused by the co-effects of the nanoparticles with the evanescent field of primary plasmons excited by the light source. This interaction causes excitation of secondary concentric plasmon waves localized in a few μm. The radiation of these secondary waves provides the light spot on the image, which can be observed by appropriate image processing. Individual particles having a size of less than 40 nm can be detected with such an assembly.

It is important to note that surfaces of several square millimeters can be simultaneously monitored. This provides the possibility to detect very low particle concentrations because the number of particles binding to the surface is proportional to the surface area. It is important with the assembly, that the particles are very close below the surface with a distance of less than 200 nm or even touch it. The assembly is suitable, for example, for the use in virologic research and for the detection of viruses at public areas. Also, the method can be used for highly sensitive clinic diagnostics.

According to the invention, the change of the reflectivity of a sensor surface is observed which is caused by a particle. In a preferred modification of the invention, this change is localized within a few $\mu m^2$ and has the form of a step on the reflectivity versus time dependence. The change is measured at a previously unknown position and at an unknown point in time. The position and the point in time are to be found individually during the measurement for each particle.

With common SPR-imaging methods, the signal is measured at a previously well defined, relatively large spot (>100×100 $\mu m^2$). Receptors are applied with such known methods at the spot and a bonding is expected. The signal integrated over the whole spot continuously increases proportionally to the layer thickness of the bound particles or molecules. A surface is used as a sensor which ensures a strong change of the reflectivity due to the change of the diffraction index.

Such a surface with strong change of the reflectivity can be realized by a gold layer in a Kretschmann assembly. In a Kretschmann assembly the reflectivity depends very much from the diffraction index of the medium in contact with the gold layer if the incident angle is near the resonance angle.

If a particle is bound to the surface, the reflectivity in the vicinity of the particle changes. Such a change reveals itself as a change of brightness at the corresponding position of the image. The change caused by an individual nanoparticle should be small and cannot be observed according to common notion. It is an object of the invention that such a change can be detected with modern techniques and appropriate image processing also for dielectric particles which are smaller than 40 nm. Contrary to common SPR imaging methods, the corresponding spots are localized in few $\mu m^2$ and the position where the signal should be detected cannot be predefined and must be found during the measurement.

The selectivity of the detection is, like in common SPR imaging methods, ensured by the selectivity of the bounding of particles to receptors at the sensor surface.

As the changes of reflectivity are depending on the size and the refraction index of the particle, they can be used for the characterization of the particle.

Alternatively, the surface with strong changes of the reflectivity can be realized by periodic structures enabling plasmon excitation. Also, antireflection coated glass or crystal surfaces are suitable. The antireflection coated coating is broken by the particles and the reflectivity in the environment increases. In a further, alternative modification of the invention, the surface with a strong change of the reflectivity is realized by a surface with metallic nanoparticles enabling the excitation of localized plasmon resonance. Such metallic nanoparticles serve as sensor particles. Near the resonance, scattering at a particle depends on the refraction index. If a small particle or virus is bound to the sensor particle, the reflectivity of the sensor surface changes at this point. Finally, the surface with strong changes of the reflectivity can be realized by a multi-layer structure where surface plasmon resonance can be excited by so called optical crystals.

Further modifications of the invention are subject matter of the subclaims. An embodiment is described below in greater detail with reference to the accompanying drawings.

DESCRIPTION OF THE EMBODIMENT

Figure 1:
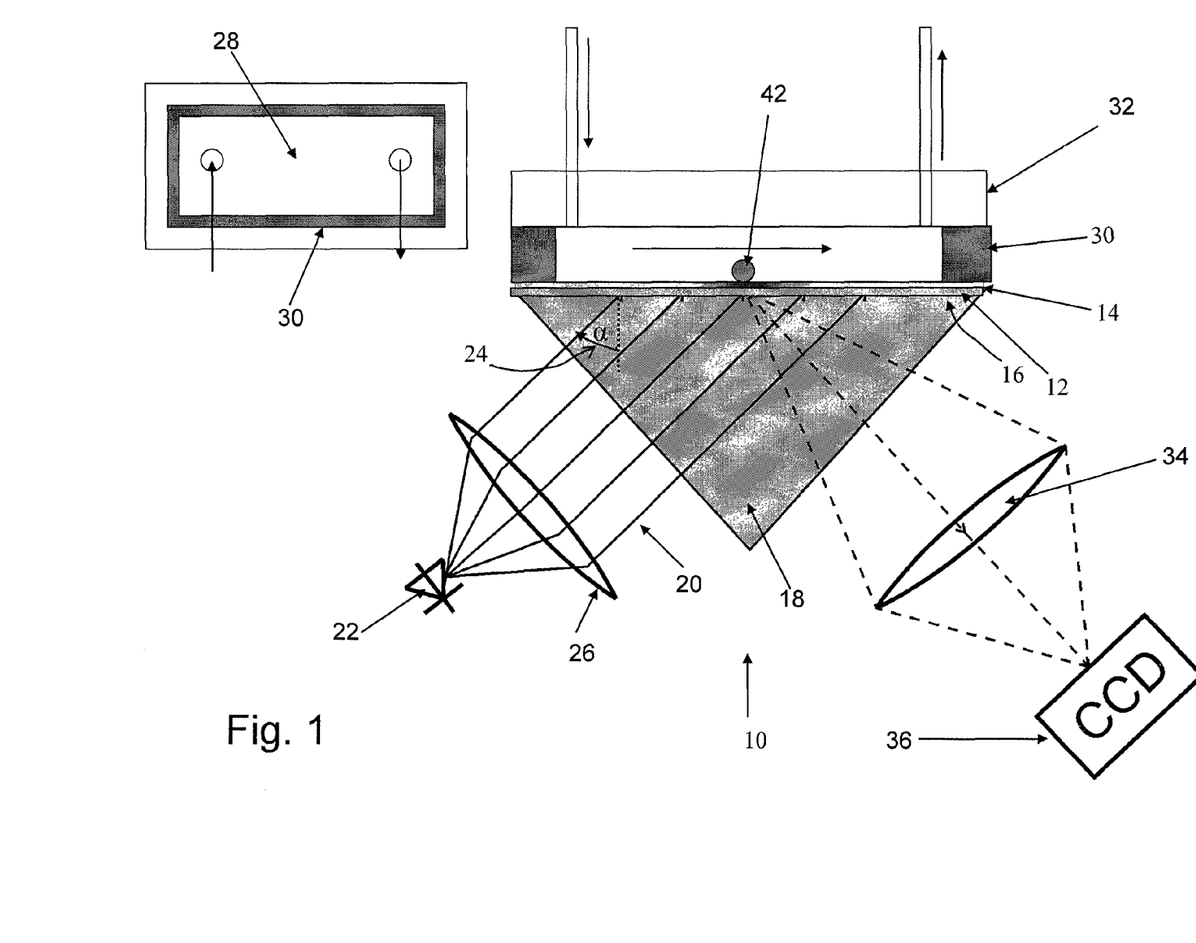
FIG. 1 is a schematic representation of a Kretschmann assembly for the detection of nanoparticles and viruses.
Figure 2:
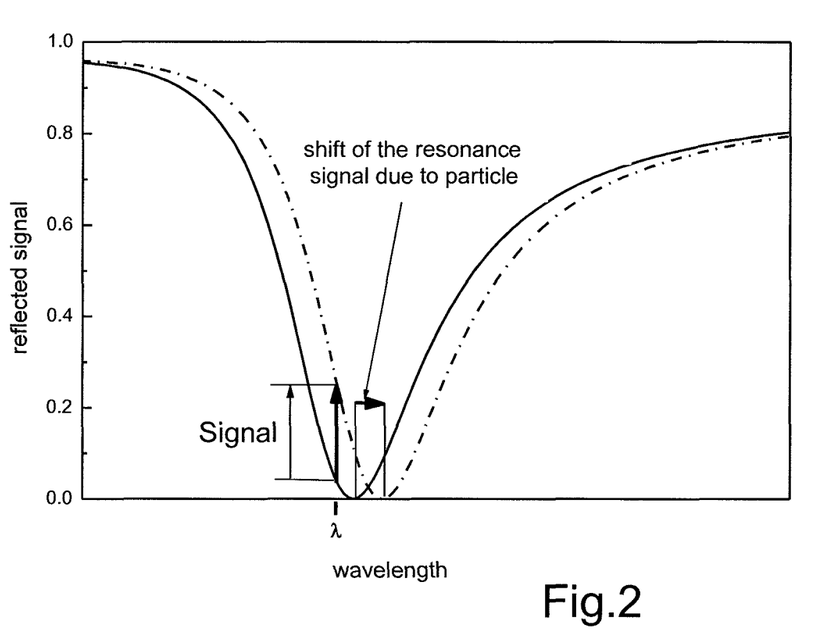
FIG. 2 shows the graph of a reflection signal near the resonance wavelength with and without a particle.

FIG. 1 shows a Kretschmann assembly in imaging configuration which is generally denoted with numeral 10. Such an assembly 10, as such, is known. The way of operation of a surface plasmon spectrometer, therefore, need not be described here in greater detail. A glass plate 12 is coated with a 50 nm gold layer 14. The side 16 of the glass plate 12 opposite to the gold layer 14 is fixed to a prism 18. Immersion oil is used for fixing and improving the optical contact.

The gold layer 14 is illuminated with radiation 20 from a superluminescent diode 22. An example for a suitable diode 22 is a QSDM-680-9 by Qphotonix emitting at a wavelength of about 670 nm, in the visible range. The illumination is effected through prism 18 with fixed incident angle 24. Contrary to a Laser as a radiation source, a superluminescent diode has no irregularities on the illuminated surface (speckles). The incident angle 24 is selected on the left side of the resonance minimum, i.e. with a smaller angle.

For the generation of a parallel radiation bundle, a lens 26 is used. It is understood that a curved mirror may also be used here.

A sample volume for liquids in the form of a flow cell 28 is arranged at the gold layer. The flow cell 28 is formed by a 1 mm thick, rectangular PDMS-seal 30. The back portion of the flow cell 28 consists of a Plexiglas plate 32 which forms the back surface of the flow cell 28. Furthermore, an inlet and an outlet in the form of tubes are provided at the flow cell 28. The volume of the flow cell 28 is about 300 μL.

The glass surface of the plate 12 forms a sensor surface. The sensor surface is imaged on a Charge Coupled Device (CCD) detector 36 with a standard Minolta Photo objective 30. The aperture of the objective 34 is 1/1.7. The CCD detector is a Cappa-100 CCD camera with a pixel size of 6.45×6.45 μm. The saturation capacity of the detector is 40,000 electrons per pixel. The detector 36 has a surface of ~1000×1000 Pixel. With a 7× enlargement, a pixel corresponds to a sensor surface of ~1 μm. The image is compressed relatively to the optical axis in a horizontal plane (p-plane) due to the increase of the sensor surface. Here, a pixel size corresponds to a sensor surface of ~1.4 μm. The increase also causes a significant limitation of the range of the sensor surface for which a sharp image can be obtained.

For the observation of particles, the images are read out with a rate of up to 100 images/second. The images are stored and evaluated.

In a well working embodiment, the readout frequency is 40 images/second. The average of 10 images is calculated. For this purpose, the average of the intensity is calculated for each pixel and stored for further processing.

The intensity distribution of the original image is very inhomogeneous. This is due to the high sensitivity of the sensor surface regarding small irregularities on the surface. Generally, many points can be seen having a deviation from an average value of up to 70%. Local inhomogenities of ±10% within a 20 μm spot on the sensor surface is typical for the remaining image. This intensity distribution is relatively stable in time. In order to reduce the inhomogenity, a normalizing step is applied. A reference image is generated by averaging over a period of time 38 (FIG. 3) where there is no particle suspension. The intensity in each pixel in the subsequent images 40 is normalized with the average value in the reference image for each pixel. Thereby a local inhomogenity in the corrected image is achieved which does not exceed ±1%.

Figure 3:
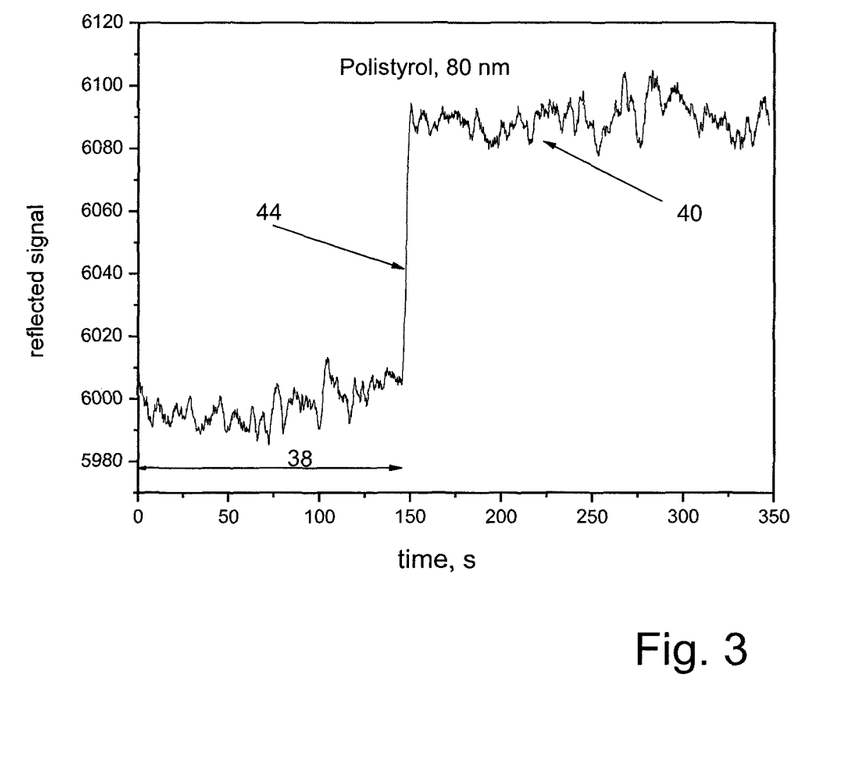
FIG. 3 shows the time dependence of a signal in a period of time where a particle is bound.
Figure 4:
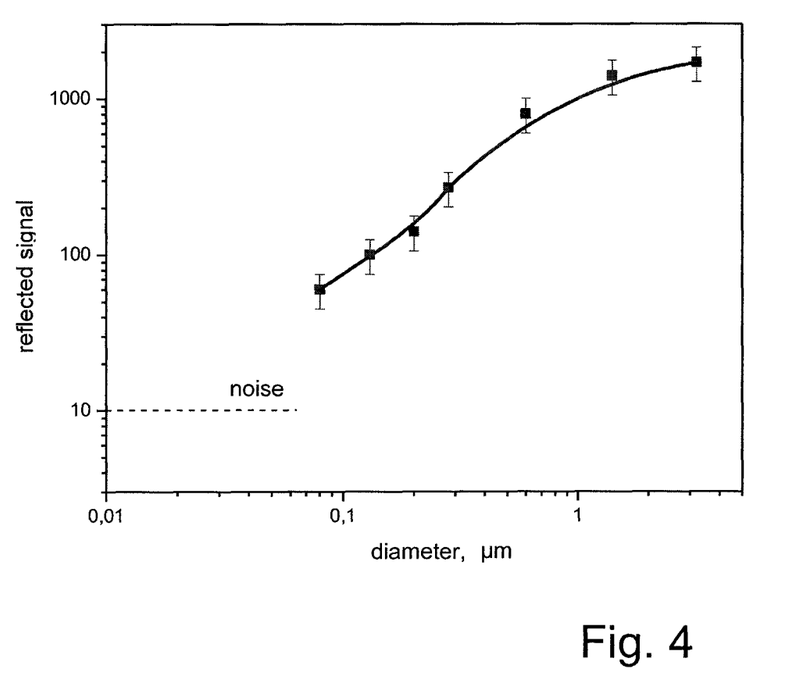
FIG. 4 shows the dependence of the signal of the particle diameter.

The bonding of a particle 42 (FIG. 1) at the sensor surface 12 causes a saltatory intensity change 44 (FIG. 3) on the corresponding pixels. Such a step 44 is integrated over all pixels affected by the binding of the particle (about 12 pixels). This constitutes a signal as it is shown in FIG. 4. The value for the step 44 characterizes the bound particle 42.

The shot noise is the essential limiting factor for the minimum detectable intensity step. In order to minimize the shot noise, the product of the pixel capacity C and the read out frequency F should be maximized. With a pixel capacity of 40,000 photo electrons, only ~20,000 can be effectively used. Otherwise there will be a saturation of some pixels due to significant inhomogenities of the image.

In the present embodiment, an average of 40 images/second is integrated over 10 pixels. Thereby, $2\times10^6$ electrons are accumulated in the surface corresponding to the bound particle. This corresponds to a shot noise of $7\times10^4$. With the present method, steps in the order of $10^{-3}$ can be detected. This means that shot noise is the limiting factor.

Figure 5:
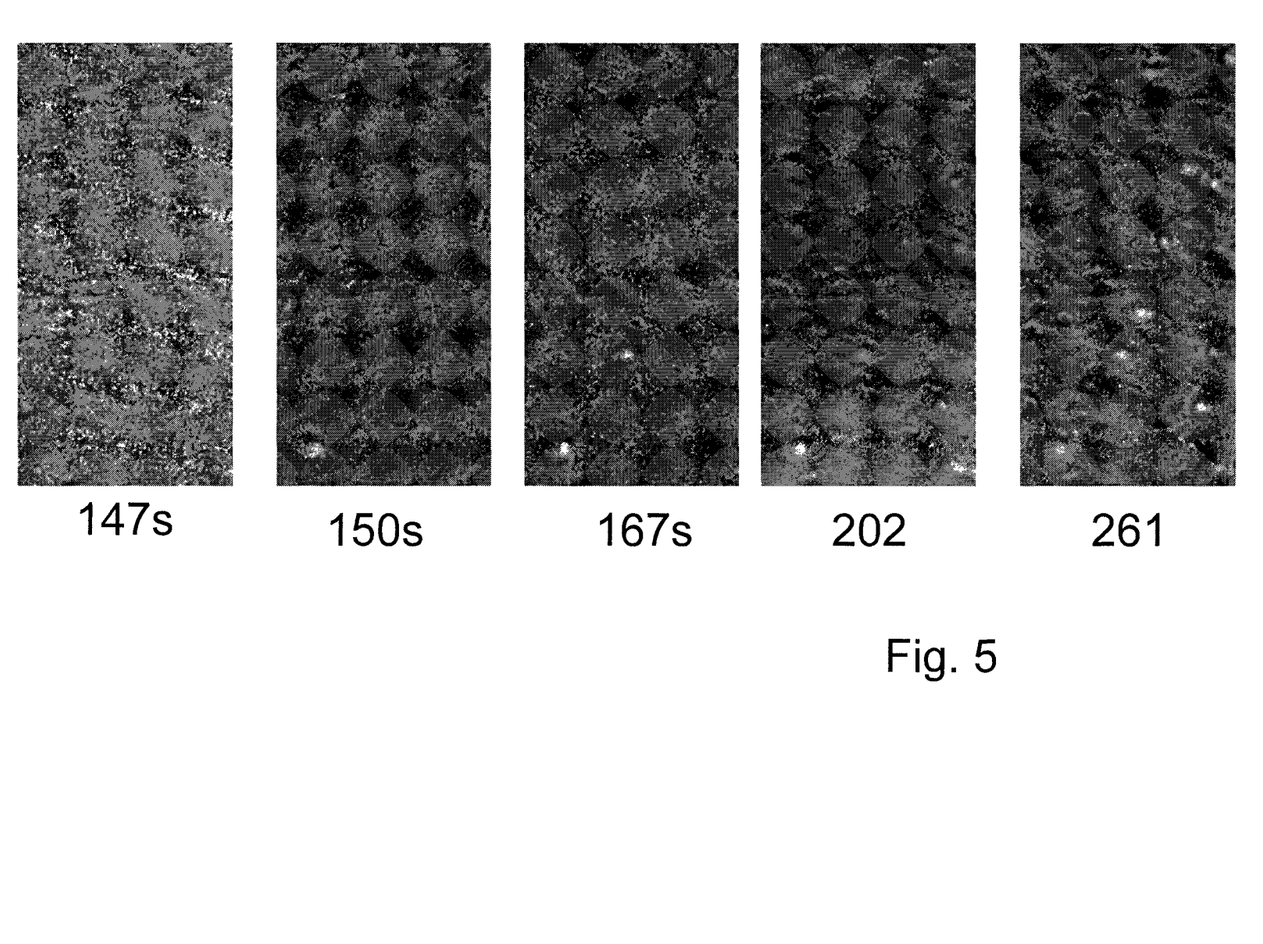
FIG. 5 shows the image of an observed surface after various observation periods for Polystyol particles having a diameter of 0.08 μm.
Figure 6:
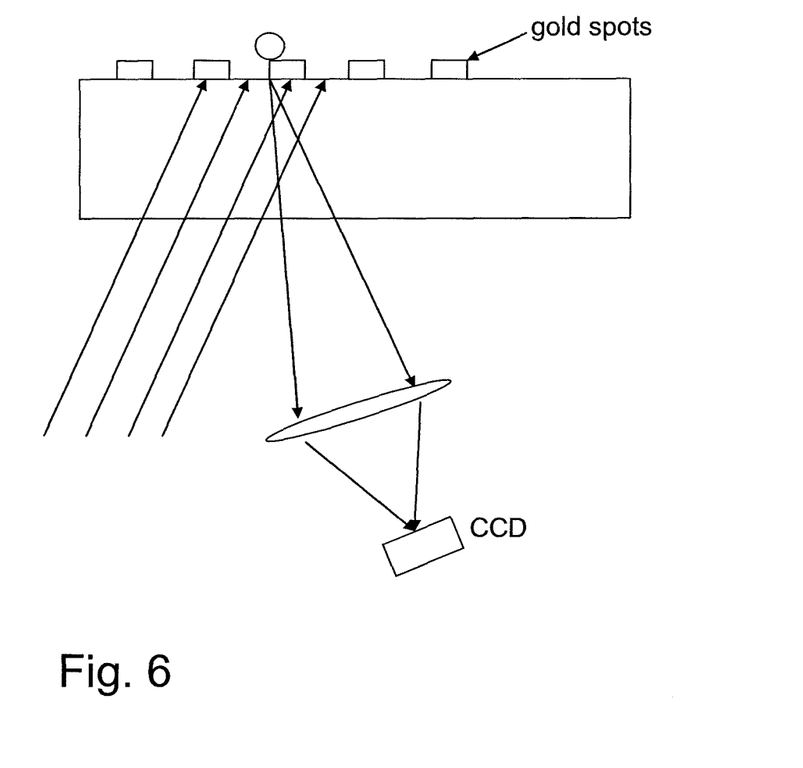
FIG. 6 is a schematic representation of an assembly with regular structures in the form of gold spots for the detection of nanoparticles and viruses.

The images in FIG. 5 were detected with a CCD camera 36. The binding of particles can be directly observed on subsequent images. The particles were injected into the sample chamber at time 140 seconds as shown in FIG. 3. The images in FIG. 5 were detected at the times indicated below the images.

In order to quantify the signal of a particle, the time dependence of the intensity in the vicinity of the particle is measured, as it is shown in FIG. 3. The value of the step is taken as the signal which characterizes the size of the bound particle. The dependency of the signal from the particle size can be seen in FIG. 4.

What is claimed is:

1. A surface plasmon resonance microscope, comprising
   a radiation source emitting essentially monochromatic radiation,
   a sensor surface reflecting said essentially monochromatic radiation with a reflectivity to obtain a reflected radiation with an intensity,
   an optical assembly for illuminating said sensor surface with said radiation emitted by said radiation source in such a way that surface plasmons are generated in said sensor surface,
   a detector with a plurality of detector elements detecting said intensity of said reflected radiation, and
   an optical assembly for imaging said radiation reflected by said sensor surface on said detector
   wherein
   said resolution of said observing optical assembly and of said detector are higher than the diffraction-limited resolution which can be obtained with the radiation source achievable under classical conditions,
   a change of said reflectivity caused by a particle at said sensor surface is observed,
   the time dependency of said intensity in the range of the image of the particle is measured to quantify the signal of a particle, wherein the bonding of the particle at the sensor surface causes a saltatory intensity change at the corresponding image points, and
   the signal is normalized with respect to a reference image which is obtained by calculating the average image over a period of time before the particle is bound.

2. A surface plasmon resonance microscope according to claim 1, and further comprising a sensor surface in Kretschmann-arrangement.

3. A surface plasmon resonance microscope, comprising
   a super luminescence diode forming a radiation source emitting essentially monochromatic radiation,
   a sensor surface reflecting said essentially monochromatic radiation with a reflectivity to obtain a reflected radiation with an intensity,
   an optical assembly for illuminating said sensor surface with said radiation emitted by said radiation source in such a way that surface plasmons are generated in said sensor surface,
   a detector with a plurality of detector elements detecting said intensity of said reflected radiation, and
   an optical assembly for imaging said radiation reflected by said sensor surface on said detector
   wherein
   said resolution of said observing optical assembly and of said detector are higher than the diffraction-limited resolution which can be obtained with the radiation source achievable under classical conditions,
   a change of said reflectivity caused by a particle at said sensor surface is observed,
   the time dependency of said intensity in the range of the image of the particle is measured to quantify the signal of a particle, wherein the bonding of the particle at the sensor surface causes a saltatory intensity change at the corresponding image points, and the signal is normalized with respect to a reference image which is obtained by calculating the average image over a period of time before the particle is bound.

4. A surface plasmon resonance microscope according to claim 1, wherein said sensor surface is coated with a gold layer.

5. A surface plasmon resonance microscope according to claim 1, and further comprising means for establishing a contact between observed particles and the sensor surface.

6. A surface plasmon resonance microscope according to claim 1, wherein said sensor surface is a surface with a strong change of said reflectivity generated by periodic structures enabling plasmon excitation.

7. A surface plasmon resonance microscope according to claim 1, wherein said sensor surface is an antireflection coated glass or crystal surface with a strong change of said reflectivity upon binding particles.

8. A surface plasmon resonance microscope according to claim 1, wherein said sensor surface is a surface with metallic nanoparticles with a strong change of said reflectivity upon binding particles enabling an excitation of localized plasmon resonance at the wavelength of said radiation source.

9. A surface plasmon resonance microscope according to claim 1, wherein said sensor surface is an optical multi-layer structure where surface plasmon resonance can be excited.

10. A surface plasmon resonance microscope, comprising
a radiation source emitting essentially monochromatic radiation,
a sensor surface reflecting said essentially monochromatic radiation with a reflectivity to obtain a reflected radiation with an intensity,
an optical assembly for illuminating said sensor surface with said radiation emitted by said radiation source in such a way that surface plasmons are generated in said sensor surface,
a detector with a plurality of detector elements detecting said intensity of said reflected radiation, and
an optical assembly for imaging said radiation reflected by said sensor surface on said detector
wherein
said resolution of said observing optical assembly and of said detector are higher than the diffraction-limited resolution which can be obtained with the radiation source achievable under classical conditions,
a change of said reflectivity caused by a particle at said sensor surface is observed,
the time dependency of said intensity in the range of the image of the particle is measured to quantify the signal of a particle, wherein the bonding of the particle at the sensor surface causes a saltatory intensity change at the corresponding image points,
the signal is normalized with respect to a reference image which is obtained by calculating the average image over a period of time before the particle is bound
said detector is a Charge Coupled Device for detection of a plurality of time subsequent intensity signals for each pixel, and
processing means are provided adapted to generate time average values for the reduction of shot noise.

11. A surface plasmon resonance spectroscope according to claim 1, wherein said bound particle causes a saltatory local change of the reflectivity in the vicinity of the binding point providing the measuring signal, whereby the position, as well as point in time of the signal appearing are not previously known and are to be found during the detection procedure.

12. Use of a surface plasmon resonance microscope according to claim 1 in virologic research, with the detection of viruses in public areas or in highly sensitive clinical diagnostics.

13. Method for the optical detection of individual nano particles on two-dimensional sensor surfaces by means of surface plasmon resonance spectroscopy, comprising the steps of:
(a) illuminating said sensor surface with radiation from a monochromatic radiation source in such a way that surface plasmons are generated in said sensor surface,
(b) introducing particles for observation on said sensor surface or in an immediate near range of said sensor surface, and
(c) detecting said radiation from said sensor surface with a detector with a plurality of detector elements,
wherein
(d) said particles are observed with a resolution which is higher than the diffraction-limited resolution obtainable by optical microscopy with said radiation source,
(e) said change of said reflectivity which is caused by a particle can be observed at said sensor surface,
(f) the time dependency of said intensity in the range of said image of said particle is measured to quantify said signal of a particle, wherein the bonding of said particle at said sensor surface has a saltatory intensity change at the corresponding image points, and
(i) said signal is normalized with respect to a reference image which is obtained by calculating the average over a period of time before said particle is bound.

* * * * *